US012672824B2

(12) United States Patent
Watanabe et al.

(10) Patent No.: US 12,672,824 B2
(45) Date of Patent: Jul. 7, 2026

(54) WEARABLE DEVICE

(71) Applicant: NTT, Inc., Tokyo (JP)

(72) Inventors: Kento Watanabe, Tokyo (JP); Kenichi Matsunaga, Tokyo (JP); Yuki Hashimoto, Tokyo (JP); Takako Ishihara, Tokyo (JP)

(73) Assignee: NTT, INC., Tokyo (JP)

( * ) Notice: Subject to any disclaimer, the term of this patent is extended or adjusted under 35 U.S.C. 154(b) by 315 days.

(21) Appl. No.: 18/573,275

(22) PCT Filed: Jun. 30, 2021

(86) PCT No.: PCT/JP2021/024786
§ 371 (c)(1),
(2) Date: Dec. 21, 2023

(87) PCT Pub. No.: WO2023/276055
PCT Pub. Date: Jan. 5, 2023

(65) Prior Publication Data
US 2024/0285234 A1 Aug. 29, 2024

(51) Int. Cl.
*A61B 5/00* (2006.01)
*G06F 1/16* (2006.01)
*H04B 1/3827* (2015.01)

(52) U.S. Cl.
CPC ............ *A61B 5/6802* (2013.01); *G06F 1/163* (2013.01); *H04B 1/3827* (2013.01)

(58) Field of Classification Search
CPC ...... A61B 5/6802; G06F 1/163; H04B 1/3827
USPC ......................................................... 600/301
See application file for complete search history.

(56) References Cited

U.S. PATENT DOCUMENTS

| | | | | | |
|---|---|---|---|---|---|
| 8,287,451 B2 * | 10/2012 | Hu | ....................... | A61B 5/0002 | |
| | | | | 600/549 | |
| 2016/0192857 A1 * | 7/2016 | Lee | ...................... | A61B 5/6802 | |
| | | | | 600/382 | |

OTHER PUBLICATIONS

Naoko Kasaif et al., "Development of Functional Textile "hitoe": Wearable Electrodes for Monitoring Hman Vital Signals," Institute of Electronics, Information and Communication Engineers, 2017, 15 pages, Summer Issue, No. 41.
Changhyun Pang et al., "Recent Advances in Flexible Sensors for Wearable and Implantable Devices," Journal of Applied Polymer Science, Jun. 2013, 13 pages, vol. 130, No. 3, Wiley Periodicals.

* cited by examiner

*Primary Examiner* — Nadia A Mahmood
(74) *Attorney, Agent, or Firm* — Slater Matsil, LLP

(57) ABSTRACT

An embodiment is a device including a substrate, the substrate being flexible. The device further comprises an electrode configured to be in contact with a living body, a circuit connected to the electrode via an electric wiring, a wireless transceiver connected to the circuit and configured to transmit and receive signals, a power supply configured to supply electric power to the circuit and the wireless transceiver, and a battery connected to the power supply, where the electrode, the circuit, the wireless transceiver, the power supply and the battery are mounted on the substrate, and the substrate is configured to be deformed to make the wireless transceiver arranged away from the living body when attached to the living body.

20 Claims, 10 Drawing Sheets

WEARABLE DEVICE

CROSS-REFERENCE TO RELATED APPLICATIONS

This application is a national phase entry of PCT Application No. PCT/JP2021/024786, filed on Jun. 30, 2021, which application is hereby incorporated herein by reference.

TECHNICAL FIELD

The present disclosure relates to a wearable device that transmits and receives signals via wireless communication.

BACKGROUND

The biological signals are measured in fitness, health care, and medical fields, and the like, and wearable devices are used for the measurement. The wearable devices are used in various forms such as a wristwatch, a wristband-type, a ring-type, a wear-type such as clothing, and an attachment-type that is directly attached to a body surface. In the wearable devices, the wear-type and the attachment-type devices have attracted attention and been developed (Non Patent Literature 1 and Non Patent Literature 2).

CITATION LIST

Non Patent Literature

Non Patent Literature 1: Nahoko Kasai, Takayuki Oga-sawara, Hiroshi Nakashima, and Shingo Tsukada, "Development and practical use of functional material 'hitoe' that enables biological information measurement just by being worn" Communication Society Magazine, 2017, Vol. 11, No. 1, pp. 17-23, The Institute of Electronics, Information and Communication Engineers.
Non Patent Literature 2: Pang, C., Lee, C. and Suh, K.-Y. (2013), Recent advances in flexible sensors for wearable and implantable devices. J. Appl. Polym. Sci., 130: 1429-1441. https://doi.org/10.1002/app.39461

SUMMARY

Technical Problem

Unfortunately, the device unit is packaged alone, which leads to a concern that the size thereof as a whole, and particularly in the height direction becomes larger.

Since the entire load of the device needs to be supported by the contact (attachment) portion between the wearable device and the measurement target (human body), it is necessary to strengthen the adhesive force and increase the attachment area to prevent the device from coming off the measurement target. This gives discomfort to the user who is the target, resulting in a concern about the attachability thereof.

Solution to Problem

In order to solve the above-described concern, a wearable device according to embodiments of the present invention includes a substrate with flexibility, and includes, on the substrate, an electrode unit that is in contact with a living body, a circuit unit connected to the electrode unit via an electric wiring, a wireless communication unit that is connected to the circuit unit and transmits and receives a signal, a power supply unit that supplies electric power to the circuit unit and the wireless communication unit, and a battery unit connected to the power supply unit, in which the substrate is deformed to make the wireless communication unit arranged away from the living body when attached to the living body.

Advantageous Effects of Embodiments of the Invention

According to embodiments of the present invention, it is possible to provide a wearable device that secures the quality of wireless communication and is excellent in the attachability.

DETAILED DESCRIPTION OF ILLUSTRATIVE EMBODIMENTS

For measurement of biological signals and actuation such as vibration and electrical stimulation via a wearable device, it is important to reduce inhibition of behavior and discomfort of a human who is a measurement target while maintaining high-precision signal measurement.

As the wearable device, a flexible device that is bendable using a stretchable and flexible material is used.

In the wearable device, wireless communication is used for transmission of acquired data. Here, in a case where the substrate of the wearable device is a rigid substrate that is used in a wristband-type or the like, sufficient communication quality can be maintained by securing a circuit ground that is necessary for antenna operation and the like.

On the other hand, in a case where the substrate of the wearable device is a flexible substrate and the flexible substrate is attached to a human body surface (skin) for its use, antenna performance cannot be sufficiently exhibited due to scattering and absorption of radio waves by the human body, resulting in a concern that a communication distance of radio waves is deteriorated.

Thus, in the structure of the conventional wearable device, the attachment unit to which an electrode is connected and the device unit including an element for wireless communication are configured separately from each other, and are physically and electrically connected to each other via a snap button or the like. In this structure, the quality of wireless communication is secured by not bringing the device unit into direct contact with the human body surface.

First Embodiment

Figure 1:
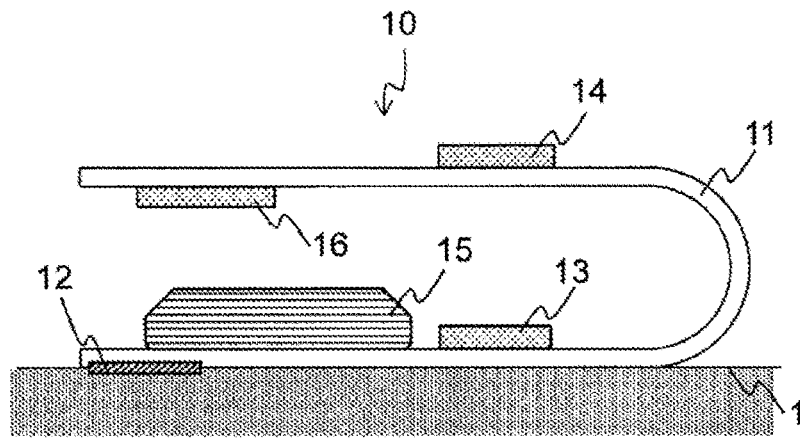
FIG. 1 is a schematic side cross-sectional view illustrating a configuration of a wearable device according to a first embodiment of the present invention.

A wearable device according to a first embodiment of the present invention will be described with reference to FIG. 1. Configuration of Wearable Device As illustrated in FIG. 1, a wearable device 10 according to the present embodiment includes a substrate 11, an electrode unit 12, a circuit unit 13, a wireless communication unit 14, a battery unit 15, and a power supply unit 16, which are connected each other via an electric wiring 17 (not illustrated).

The substrate 11 is a flexible substrate having a double-sided structure with flexibility, and has a bendable flip structure. FIG. 1 illustrates a state in which the substrate 11 is bent. The substrate 11 may be a single layer or a multilayer.

The electrode unit 12 is in contact with a surface 1 of a target (a living body such as a human) and is connected to the circuit unit 13 via the electric wiring 17. The electrode unit 12 may be one or more.

The circuit unit 13 includes a sensor unit or an actuator unit, and detects biological signals or supplies vibration or stimulation via the electrode unit 12.

The wireless communication unit 14 is connected to the circuit unit 13 and wirelessly transmits and receives signals.

The power supply unit 16 is connected to the battery unit 15, and is connects to the circuit unit 13 and the wireless communication unit 14 to supply electric power. Here, the battery unit 15 includes a cell, a battery, or the like.

The circuit unit 13, the battery unit 15, and the power supply unit 16 are arranged on one surface of the substrate 11, and the electrode unit 12 and the wireless communication unit 14 are arranged on the other surface thereof.

As illustrated in FIG. 1, when the substrate 11 is bent, the circuit unit 13, the battery unit 15, and the power supply unit 16 on the one surface are positioned inside the substrate 11, and the electrode unit 12 and the wireless communication unit 14 on the other surface are positioned outside the substrate 11. In this manner, the electrode unit 12 is brought into contact with the surface of a living body such as the human body (body surface) 1 to be attached to a target (living body).

At this time, the wireless communication unit 14 is arranged at a position away from the body surface 1 (upper side in FIG. 1) by the space created due to bending the substrate 11. Here, the distance between the wireless communication unit 14 and the body surface 1 is preferably about 1 mm to 10 mm.

For example, when the distance between the wireless communication unit 14 and the surface of a living body (human body or the like) is about 5 mm, the radiation efficiency, which is an index of antenna performance, is improved by about 10% (A. Alomainy, Y. Hao, and D. M.

Davenport, "Parametric Study of Wearable Antennas with Varying Distances from the Body and Different On-Body Positions," in 2007 IET Seminar on Antennas and Propagation for Body-Centric Wireless Communications, April 2007, pp. 84-89, doi: 10.1049/ic:20070552).

Here, the size h in the height direction of the wearable device 10 is expressed by Expression (1) where the substrate thickness is defined as μ, the height of the component parts positioned inside the substrate 11 is defined as hin, i, and the height of the component parts positioned outside the substrate 11 is defined as hout, i when the substrate 11 is bent.

[Math. 1]

$$h = 2\mu + \max_i(h_{in,i}) + \max_i(h_{out,i}) \tag{1}$$

Here, the height direction is a direction perpendicular to surfaces of a portion that is not bent in the substrate 11.

When the substrate 11 is bent in the wearable device 10, in a case where the component parts positioned on the respective faces opposed to each other inside the substrate 11 are arranged so as to overlap each other, the size increases by the sum of the heights of the component parts overlapping each other.

Then, the size in the height direction can be reduced by the layout and arrangement in which the component parts positioned on the respective faces opposed to each other inside the substrate 11 do not spatially overlap each other when the substrate 11 is bent.

As described above, according to the wearable device according to the present embodiment, by using the flexible substrate as the substrate 11, and arranging the wireless communication unit 14 at a position physically away from the body surface 1 due to the flip structure, the influence of scattering and absorption of radio waves by the human body can be reduced, so that deterioration of the antenna performance can be mitigated.

Accordingly, the device size can be reduced, so that it is possible to reduce discomfort of the user when attached to improve the attachability of the wearable device.

Further, in the conventional structure, when the flexible substrate to be in contact with a human body or the like is deformed (bent, curved), for example, a crack may be created in solder of the device mounted on the flexible substrate, which leads to a concern about reliability.

The wearable device according to the present embodiment can improve the reliability by arranging the wireless communication unit 14 that has a high component part density away from a portion to be in contact with a human body or the like (living body).

In the present embodiment, an Ag/AgCl electrode, a cloth electrode, or the like can be used as the electrode unit 12. In addition, if the electrode structure is formed by the wiring on the flexible substrate, the cost can be reduced.

Modification

A wearable device according to a modification of the present embodiment will be described with reference to FIGS. 2A and 2B.

Figure 2A:
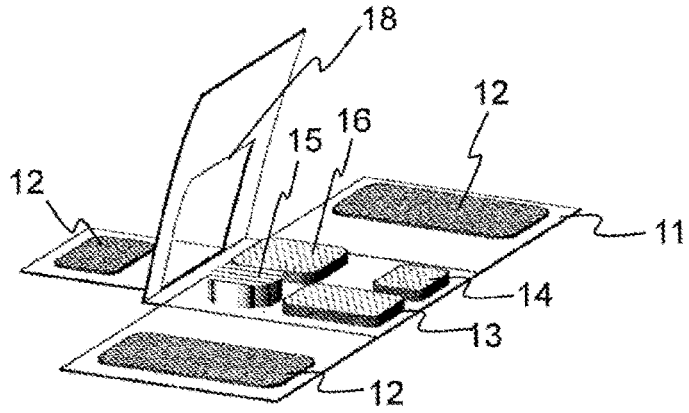
FIG. 2A is a schematic bird's-eye view illustrating a configuration of a modification of a wearable device according to the first embodiment of the present invention.
Figure 2B:
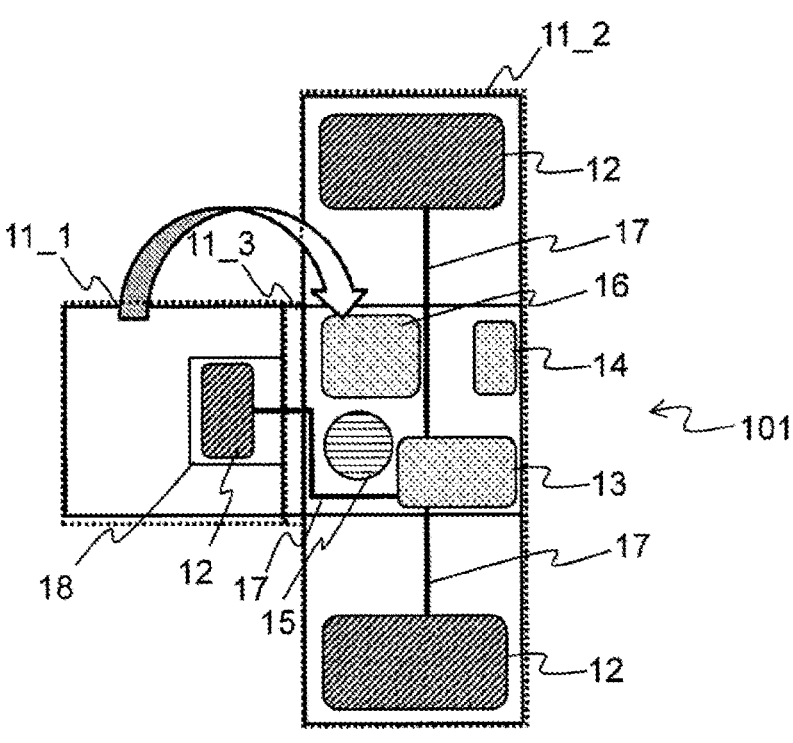
FIG. 2B is a diagram for illustrating a configuration of the modification of the wearable device according to the first embodiment of the present invention.
Figure 2B:
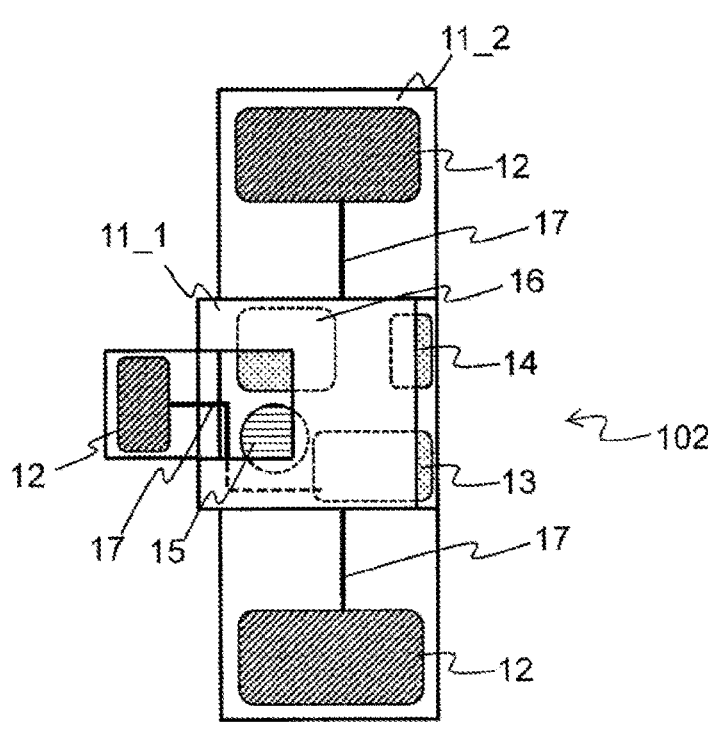

In the wearable device according to the present modification, as illustrated in FIGS. 2A and 2B, the substrate 11 is bent such that three sides of a quadrangular region 18, which is a part of the substrate 11, are cut and only one side thereof is connected to the substrate 11.

FIG. 2B illustrates a developed plan view 101 of the wearable device according to the present modification and a plan view 102 of the wearable device in a state of being bent and attached to the body surface as viewed from the body surface side.

The substrate 11 has a T-shape and includes a base 11_1, an extension 11_2, and a connection 11_3. The base 11_1 and the extension 11_2 are connected to each other through the connection 11_3.

In the substrate 11, three sides of the quadrangular region 18, which is a part of the base 11_1, are cut and only one side thereof is connected to the connection 11_3. The electrode unit 12 is arranged on one surface of the quadrangular region 18.

In the extension 11_2, on one surface thereof, the electrode units 12 are arranged in both end portions thereof, and the circuit unit 13, the battery unit 15, the power supply unit 16, and the wireless communication unit 14 are arranged in a central portion thereof.

As illustrated in the plan view 102, the base 11_1 excluding the quadrangular region 18 is bent at the connection 11_3, and the electrode unit 12 arranged in the quadrangular region 18 of the base 11_1 and the electrode units 12 arranged in both end portions of the extension 11_2 are brought into contact with the body surface 1 together with the other surface of the base 11_1 to be attached on the object (living body).

At this time, since the substrate 11 is bent, the central portion of the extension 11_2 in which the wireless communication unit 14 and the like are arranged is positioned above the base 11_1, that is, positioned away from the body surface 1.

As described above, in the wearable device, while the electrode units 12 can be brought into contact with the body surface (skin) 1, the wireless communication unit 14 can be arranged away from the body surface 1.

Thus, according to the wearable device according to the present modification, the influence of scattering and absorption of radio waves by the human body is reduced, so that effects similar to those of the first embodiment are obtained.

In this configuration, the electrode unit 12 can be arranged in the quadrangular region 18, so that a total of three electrodes can be attached to the body surface.

In addition, the flip structure of the substrate 11 may have a configuration of three or more layers such as three-fold.

Second Embodiment

A wearable device according to a second embodiment of the present invention will be described with reference to FIGS. 3 and 4.
Configuration of Wearable Device A wearable device 20 according to the present embodiment is different from the device according to the first embodiment in arrangement of a wireless communication unit. The other configurations are substantially similar to those of the first embodiment.

Figure 3:
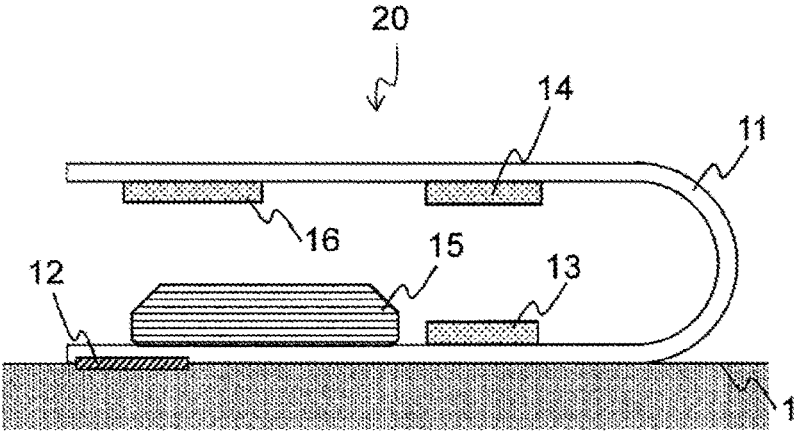
FIG. 3 is a schematic side cross-sectional view illustrating an example of a configuration of the conventional wearable device.

In the wearable device 20, as illustrated in FIG. 3, the circuit unit 13, the battery unit 15, the power supply unit 16, and the wireless communication unit 14 are arranged on one surface of the substrate 11, and the electrode unit 12 is arranged on the other surface thereof.

As illustrated in FIG. 3, when the substrate 11 is bent, the circuit unit 13, the battery unit 15, the power supply unit 16, and the wireless communication unit 14 on the one surface are positioned inside the substrate 11, and the electrode unit 12 on the other surface are positioned outside the substrate

11. In this manner, the electrode unit 12 is brought into contact with the surface of a living body such as the human body (body surface) 1 to be attached to a target (living body).

At this time, the wireless communication unit 14 is arranged at a position away from the body surface 1 (upper side in FIG. 1) by the space created due to bending the substrate 11.

Figure 4:
FIG. 4 is a schematic side cross-sectional view illustrating a configuration of a wearable device according to a second embodiment of the present invention.

In a case where a flexible substrate with high flexibility is used in the conventional wearable device, as illustrated in FIG. 4, there is a case where a hard material 21 is combined therewith to suppress deformation (bent, curve, and the like) of the substrate 11, and component parts (elements, devices) 22 are mounted on a front surface (one surface) of the substrate 11.

In this case, since a back surface (the other surface, lower surface in FIG. 4) of the flexible substrate 11 needs to be flat to be combined with the hard material 21, the component parts cannot be mounted on this surface.

As described above, in the wearable device 20, since the components (component parts) other than the electrode unit 12 are arranged on the one surface, the substrate 11 can be combined with a hard material.

Here, the electrode unit 12 can be attached to the other surface with a conductive adhesive or the like after the component parts other than the electrode unit 12 are mounted on the one surface. In addition, the electric wiring may be provided on the other surface.

According to the wearable device according to the present embodiment, with the configuration in which the flexible substrate with high flexibility is combined with a hard material, effects similar to those of the first embodiment can be obtained.

The component parts, which are mounted on only one surface, can be easily mounted, so that the cost in device mounting can be reduced.

In the present embodiment, by not arranging metal around the portion where the wireless communication unit 14 is arranged, and the like to keep the portion electrically open, it is possible to avoid deterioration of wireless performance even when the wearable device is attached with being in contact with a human body (skin).

In addition, the size h in the height direction of the wearable device according to the present embodiment is expressed by Expression (2).

[Math. 2]

$$h = 2\mu + \max_i(h_{in,i}) + \max_i(h_{out,i}) = 2\mu + \max_i(h_{in,i}) \tag{2}$$

As described above, the size h in the height direction of the wearable device 20 is smaller than the height in the first embodiment since no component part (wireless communication unit) is arranged outside the substrate when the substrate is bent. Accordingly, discomfort of the user can be further reduced.

Third Embodiment

A wearable device according to a third embodiment of the present invention will be described with reference to FIG. 5.
Configuration of Wearable Device FIG. 5 is a developed plan view 301 of a wearable device 30 according to the present embodiment and a plan view 302 of the wearable device 30 in a state of being bent and attached to the body surface 1 as viewed from above the body surface 1.

Figure 5:
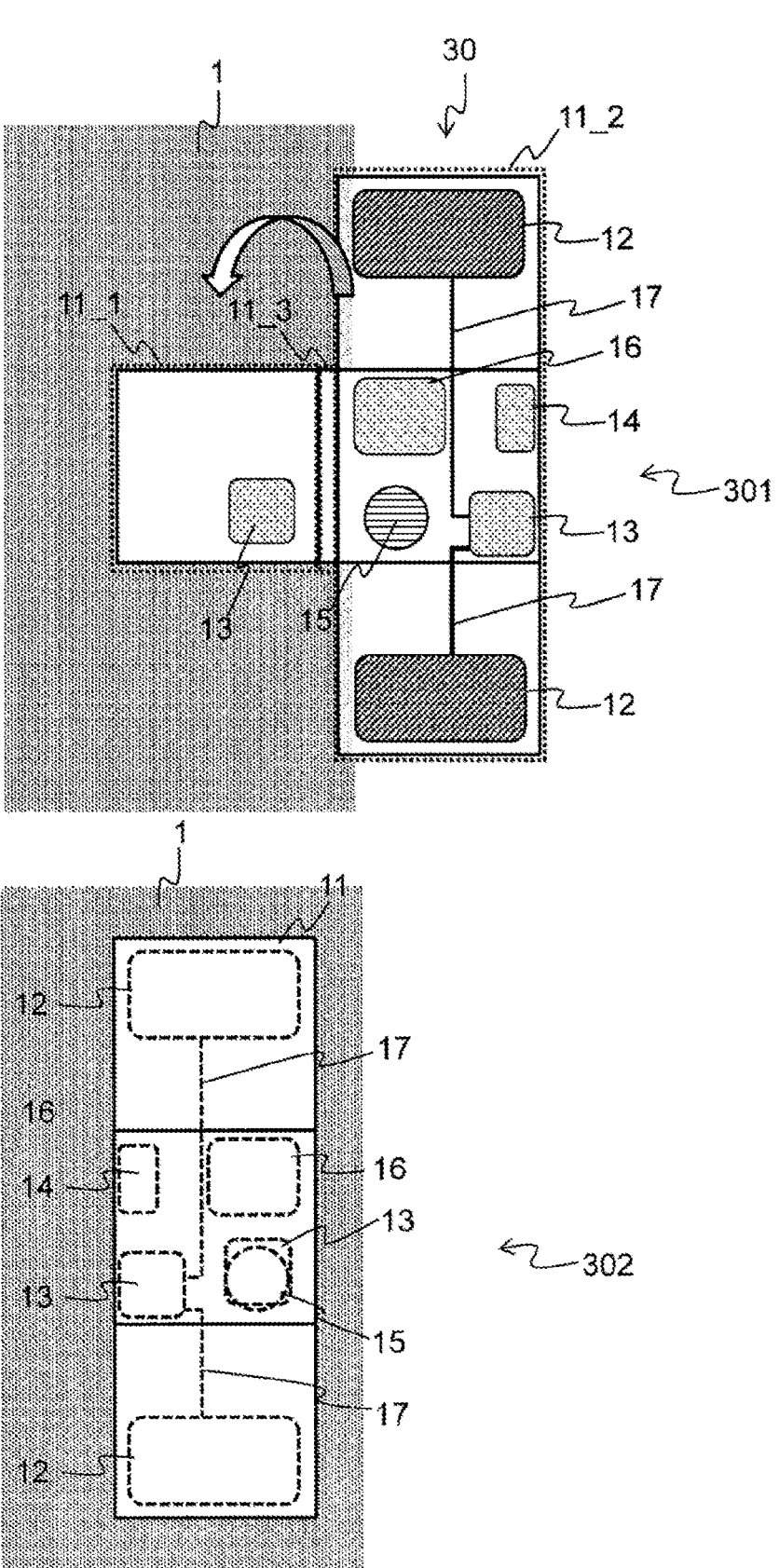
FIG. 5 is a diagram for illustrating a configuration of a wearable device according to a third embodiment of the present invention.

In the wearable device 30 according to the present embodiment, the flexible substrate 11 having a single-sided structure is used, and as illustrated in FIG. 5, the circuit unit 13, the battery unit 15, the power supply unit 16, the wireless communication unit 14, and the electrode units 12 are arranged on one surface of the substrate 11. The other configurations are substantially similar to those of the first and second embodiments.

In the wearable device 30, the substrate 11 has a T-shape and includes the base 11_1, the extension 11_2, and the connection 11_3.

The base 11_1 is a portion in contact with the body surface 1, and the circuit unit 13 is arranged on a surface (one surface) opposite to the surface in contact with the body surface 1.

In the extension 11_2, on one surface thereof, the electrode units 12 are arranged in both end portions thereof, and the circuit unit 13, the battery unit 15, the power supply unit 16, and the wireless communication unit 14 are arranged at the central portion thereof. As will be described below, the central portion of extension 11_2 is the portion that does not come into contact with a target (human body or the like) when the substrate 11 is bent.

The base 11_1 and the extension 11_2 are connected to each other through the connection 11_3.

The wearable device 30 is attached to a target (living body) by bringing the base 11_1 into contact with the body surface 1, and bending the device at the connection 11_3 to bring the electrode units 12 at both end portions of the extension 11_2 into contact with the body surface 1.

At this time, since the substrate 11 is bent, the central portion of the extension 11_2 in which the wireless communication unit 14 and the like are arranged is positioned above the base 11_1, that is, positioned away from the body surface 1.

As described above, in the wearable device 30, while the electrode units 12 can be brought into contact with the body surface (skin) 1, the wireless communication unit 14 can be arranged away from the body surface 1.

Thus, according to the wearable device according to the present embodiment, the influence of scattering and absorption of radio waves by the human body is reduced, so that effects similar to those of the first embodiment are obtained.

With the conventional technique, it is difficult to manufacture a multilayer flexible substrate having a double-sided structure as compared with a rigid substrate, and the cost is higher. On the other hand, in a case where a plurality of substrates having a single-sided structure is laminated to form a multilayer substrate, the multilayer substrate can be relatively easily manufactured. In the multilayer substrate having the single-sided structure, the uppermost surface is electrically exposed, so that the component parts can be mounted thereon. On the other hand, the lowermost surface thereof is not electrically exposed, so that the component parts cannot be mounted thereon.

In the wearable device according to the present embodiment, since all of the components (component parts) including the electrode units are arranged on only one surface, a multilayer substrate having a single-sided structure can be used therein, so that effects similar to those of the first and second embodiments can be obtained.

In addition, the manufacturing cost can be reduced.

In the present embodiment, an example in which the substrate has a T-shape and the electrodes are arranged at both end portions of the extension has been described, but the present invention is not limited thereto. For example, the electrode unit may be disposed only at one end portion of the extension.

In addition, in the present embodiment, an example in which the substrate has a T-shape has been described, but the present invention is not limited thereto. For example, the substrate may have an L-shape. In this case, the electrode unit may be arranged in only one end portion of the extension.

Fourth Embodiment

A wearable device according to a fourth embodiment of the present invention will be described with reference to FIG. 6.

Configuration of Wearable Device

A wearable device 40 according to the present embodiment is different from the devices according to the first to third embodiments in arrangement of each component (component part). The other configurations are substantially similar to those of the third embodiment.

Figure 6:
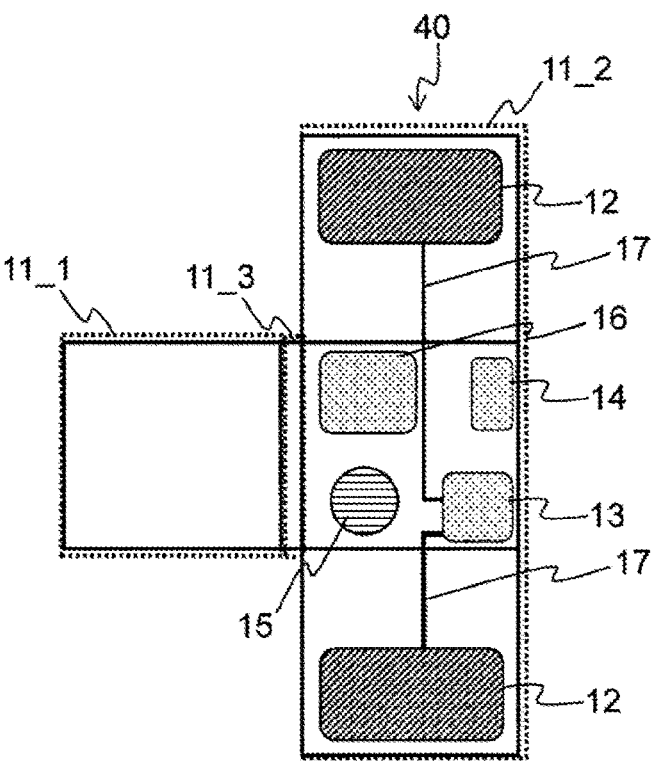
FIG. 6 is a diagram for illustrating a configuration of a wearable device according to a fourth embodiment of the present invention.

As illustrated in FIG. 6, in the extension 11_2 of the substrate 11 in the wearable device 40, the circuit unit 13, the battery unit 15, the power supply unit 16, the electrode units 12, and the wireless communication unit 14 are arranged on a surface (one surface) opposite to a surface in contact with the body surface 1.

In particular, the circuit unit 13, the battery unit 15, the power supply unit 16, and the wireless communication unit 14 other than the electrode units 12 are arranged on the one surface of a central portion of the extension 11_2, that is, the portion that does not come into contact with a target (living body such as human body) when the substrate 11 is bent.

Accordingly, the components (the circuit unit 13, the battery unit 15, the power supply unit 16, and the wireless communication unit 14) other than the electrode unit 12 are arranged at positions away from the object (living body).

In the conventional wearable device and the wearable devices according to the first to third embodiments, the components (component parts) are arranged in a portion (hereinafter, referred to as a "body surface contact portion".) to be in contact with the surface of the target (living body). In this case, since the components (component parts) are formed from a hard material, even if the components (component parts) are mounted on the flexible substrate, the flexibility is impaired. This gives discomfort to the user who is the target.

In addition, in a case where the components (component parts) are mounted on a flexible substrate with flexibility, bending stress concentrates on the components (component parts), which causes failure of the device in a short period of time.

According to the wearable device according to the present embodiment, all of the components (component parts) are arranged in the portion away from the body surface in the substrate 11 and are not arranged in the body surface contact portion (the base 11_1) due to the flip structure. This arrangement can secure the flexibility in the body surface contact portion to secure enough adhesion to the surface (body surface or the like) of the target having the curved surface.

In addition, since the components (component parts) are not arranged in the body surface contact portion, by providing a slit or the like in the body surface contact portion, the area of the body surface contact portion can be reduced. Accordingly, it is expected to reduce itching and rash of the body surface (skin).

Fifth Embodiment

A wearable device according to a fifth embodiment of the present invention will be described with reference to FIG. 7. Configuration of Wearable Device A wearable device 50 according to the present embodiment is different from the devices according to the first to fourth embodiments in arrangement of a region of an electric wiring. The other configurations are substantially similar to those of the third embodiment.

Figure 7:
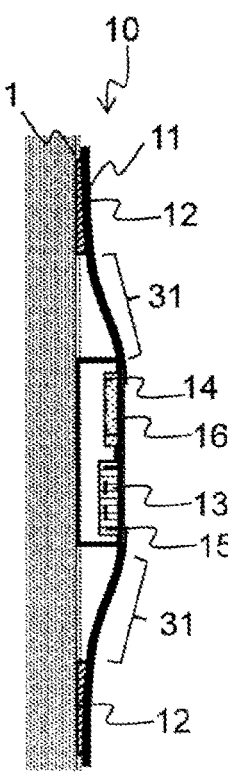
FIG. 7 is a schematic side cross-sectional view illustrating a configuration of a wearable device according to a fifth embodiment of the present invention.

In the wearable device 50, as illustrated in FIG. 7, regions where the electric wiring 17 is arranged (hereinafter, referred to as "wiring regions") 31 are provided so as to be positioned away from the target (living body) when attached.

Specifically, in the substrate 11, intermediate portions between the portion (the central portion of the extension 11_2) where the components (component parts) are arranged away from the object (living body) and the respective portions (both end portions of the extension 11_2) that include the electrode units 12 and are in contact with the target (living body) are configured not to be in contact with the object (living body) so as to form a space between the object (living body) when attached. The wiring regions 31 are arranged in the intermediate portions.

Accordingly, the wiring regions 31 can be used for a movable portion.

It is desirable to use paste type wiring mainly formed from silver in the wiring regions 31 in the wearable device 50. Accordingly, both the substrate 11 and the wiring regions 31 can have elasticity.

According to the wearable device according to the present embodiment, it is possible to reduce the contact area with the body surface with respect to the device area. In addition, the device can be attached on a curved portion or a movable portion such as a joint in a living body, and the position to be attached can be adjusted in accordance with individual differences such as body shape.

In addition, by arranging the electrodes away from each other to obtain the potential difference between the plurality of electrodes, the quality of the biological signal can be improved without increasing the contact area with the body surface.

In addition, by reducing the contact area with the body surface, a rash on the body surface and discomfort of the user can be prevented. According to this configuration, by providing any opening in the contact portion with the body surface or the wiring regions, moisture that causes stuffiness in the vicinity of the body surface can be released, so that a rash on the body surface and discomfort of the user can be prevented.

Sixth Embodiment

A wearable device according to a sixth embodiment of the present invention will be described with reference to FIGS. 8 and 9.
Configuration of Wearable Device In a wearable device 60 according to the present embodiment, the wearable device includes a component for activating the device. The other configurations are substantially similar to those of the third embodiment.

The wearable device 60 includes an activation unit in addition to the configurations in the third embodiment.

For example, an acceleration sensor is used as the activation unit. The acceleration sensor outputs an activation signal by vibration. Accordingly, inputting the vibration at the time of use can activate the device.

Figure 8:
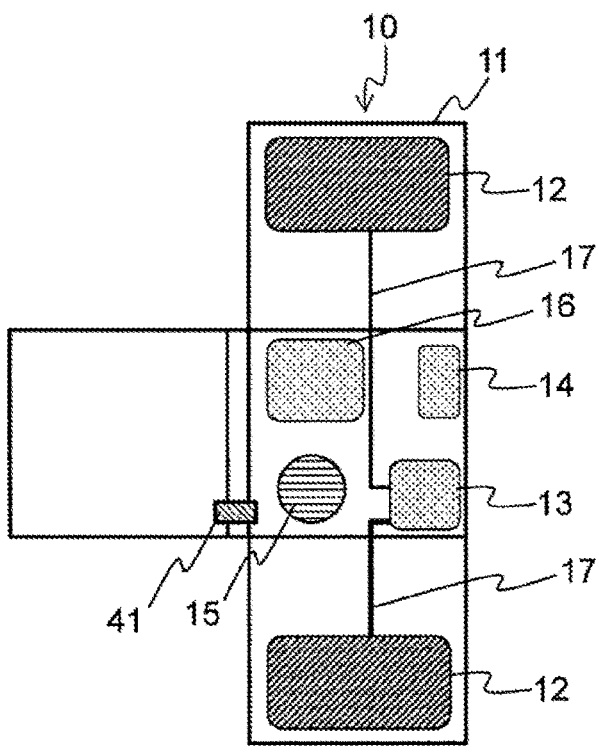
FIG. 8 is a diagram for illustrating an example of a configuration of a wearable device according to a sixth embodiment of the present invention.

Alternatively, as illustrated in FIG. 8, for example, an element 41 for bending detection is used as the activation unit. The element 41 for bending detection is arranged in a portion to be bent due to the flip structure of the substrate 11. With the element 41, it is possible to detect a change in the potential (high, low) due to bending to activate the device.

Figure 9:
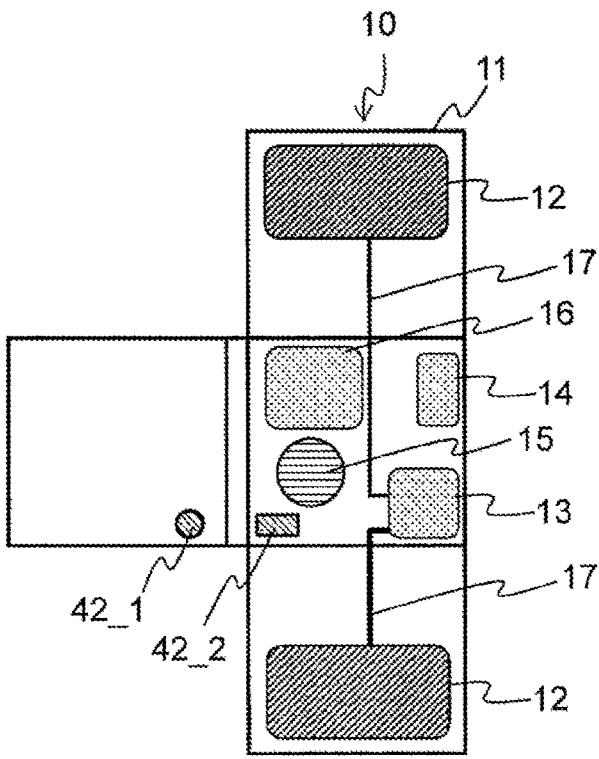
FIG. 9 is a diagram for illustrating an example of a configuration of a wearable device according to the sixth embodiment of the present invention.

Alternatively, as illustrated in FIG. 9, for example, combination of a magnet unit 42_1 and a magnetic detection unit 42_2 such as a magnetic proximity sensor, a magnetic switch or the like is used as the activation unit. The magnet unit 42_1 and the magnetic detection unit 42_2 are arranged on one surface, and are arranged such that the magnet unit 42_1 and the magnetic detection unit 42_2 that are positioned on the respective faces opposed to each other inside the substrate 11 when the substrate 11 is bent are in contact with or close to each other.

Accordingly, the substrate 11 is bent to bring the magnet unit 42_1 and the magnetic detection unit 42_2 into contact with or close to each other, whereby the device can be activated.

In this manner, the wearable device 60 can be activated by the activation unit without individually including a switch.

Since the wearable device is attached on a body surface for its use, the device requires waterproof processing. However, in a case where a physical input means such as an individual switch is provided thereto together with the waterproof processing, the manufacturing cost and the device size increase.

According to the wearable device according to the present embodiment, since it is not necessary to individually provide a switch for the activation thereof, the waterproof processing can be easily performed, so that the manufacturing cost and the device size can be reduced.

In the embodiment of the present invention, an example in which the substrate is bent to arrange the wireless communication unit at a position away from the body surface has been described, but the present invention is not limited thereto. The substrate may be curved or folded. It is only required that the substrate is deformed such that the wireless communication unit is arranged at a position away from the body surface.

The embodiment of the present invention illustrates an example of a structure, dimensions, materials, and the like of each component in the configuration, manufacturing method, and the like of the wearable device. However, the present invention is not limited thereto. Any structures, dimensions, materials, and the like that exhibit the functions to obtain the effects of the wearable device may be used.

INDUSTRIAL APPLICABILITY

The embodiments of present invention can be applied to a wireless communication system using a wearable device.

REFERENCE SIGNS LIST

1 living body
10 wearable device
11 substrate
12 electrode unit
13 circuit unit

14 wireless communication unit
15 battery unit
16 power supply unit
17 electric wiring

The invention claimed is:

1. A wearable device comprising:
a substrate, the substrate being flexible;
an electrode configured to be in contact with a living body;
a circuit connected to the electrode via an electric wiring;
a wireless transceiver connected to the circuit and configured to transmit and receive signals;
a power supply configured to supply electric power to the circuit and the wireless transceiver; and
a battery connected to the power supply, wherein:
the electrode, the circuit, the wireless transceiver, the power supply and the battery are mounted on the substrate, and
the substrate is configured to be deformed such that a first portion of the substrate is in contact with the living body and a second portion of the substrate is spaced apart from the living body, the wireless transceiver being arranged on the second portion of the substrate.

2. The wearable device of claim 1, wherein the circuit, the wireless transceiver, the power supply, and the battery are arranged on one surface of the substrate, and wherein the electrode is arranged on another surface of the substrate.

3. The wearable device of claim 1, wherein the substrate includes a base, an extension, and a connection that connects the base and the extension, wherein the electrode, the circuit, the wireless transceiver, the power supply, and the battery are arranged on one surface of the substrate, wherein another surface of the base is configured to be in contact with the living body, wherein the electrode is included in an end portion of the extension, and wherein the substrate is configured to be deformed at the connection to bring the electrode into contact with the living body.

4. The wearable device of claim 3, wherein the circuit, the wireless transceiver, the power supply, and the battery are not arranged on the base.

5. The wearable device of claim 4, wherein the electric wiring is arranged in a portion of the substrate that is not configured to be in contact with the living body.

6. The wearable device of claim 5, wherein the wearable device includes an opening in the portion where the electric wiring is arranged in the substrate.

7. The wearable device of claim 1, further comprising:
a sensor, the sensor comprising an acceleration sensor, a bending detection sensor, or a magnetic proximity sensor.

8. The wearable device of claim 7, further comprising a magnetic switch.

9. The wearable device of claim 1, wherein the electrode is formed by the electric wiring.

10. A device comprising:
a substrate;

an electrode configured to be in contact with a living body;
a circuit connected to the electrode via an electric wiring;
a wireless transceiver connected to the circuit and configured to transmit and receive signals;
a power supply configured to supply electric power to the circuit and the wireless transceiver; and
a battery connected to the power supply, the electrode, the circuit, the wireless transceiver, the power supply and the battery being mounted on the substrate, the substrate being configured to be deformed such that a first portion of the substrate is in contact with the living body and a second portion of the substrate is spaced apart from the living body, the wireless transceiver being arranged on the second portion of the substrate, the circuit, the wireless transceiver, the power supply, and the battery being arranged on one surface of the substrate, and the electrode being arranged on another surface of the substrate.

11. The device of claim 10, wherein the substrate includes a base, an extension, and a connection that connects the base and the extension, wherein the electrode is arranged at an end portion of the extension, and wherein the substrate is configured to be deformed at the connection to bring the electrode into contact with the living body.

12. The device of claim 11, wherein the circuit, the wireless transceiver, the power supply, and the battery are not arranged on the base.

13. The device of claim 10, wherein the electrode is formed by the electric wiring.

14. The device of claim 11, wherein the substrate is configured to be deformed such that the wireless transceiver is arranged away from the living body when attached to the living body.

15. The wearable device of claim 3, wherein the substrate is configured to be deformed such that the wireless transceiver is arranged away from the living body when attached to the living body.

16. The wearable device of claim 1, wherein, when the substrate is deformed, the circuit, the power supply, and the battery are positioned between opposing portions of the substrate.

17. The wearable device of claim 16, wherein component parts on respective opposing inner faces of the substrate do not spatially overlap each other when the substrate is deformed.

18. The wearable device of claim 1, wherein a distance between the wireless transceiver and the living body is between 1 mm and 10 mm when the first portion of the substrate is in contact with the living body.

19. The device of claim 10, wherein, when the substrate is deformed, the circuit, the power supply, and the battery are positioned between opposing portions of the substrate.

20. The device of claim 19, wherein component parts on respective opposing inner faces of the substrate do not spatially overlap each other when the substrate is deformed.

* * * * *